United States Patent [19]

Jin et al.

[11] Patent Number: 5,679,312
[45] Date of Patent: Oct. 21, 1997

[54] MULTIPLE STAGE SUSPENDED REACTIVE STRIPPING PROCESS AND APPARATUS

[75] Inventors: Shiyi Jin; Jitang Yuan; Zongli Zhang; Huisheng Lu; Lianshun Wang; Jinzhu Yin, all of Tianjin, China

[73] Assignees: China Petro-Chemical Corporation, Beijing; Tianjin University, Tianjin, both of China

[21] Appl. No.: 505,311

[22] PCT Filed: Feb. 16, 1994

[86] PCT No.: PCT/CN94/00012

§ 371 Date: Oct. 30, 1995

§ 102(e) Date: Oct. 30, 1995

[87] PCT Pub. No.: WO94/19079

PCT Pub. Date: Sep. 1, 1994

[30] Foreign Application Priority Data

Feb. 17, 1993 [CN] China ................... 93101418
Feb. 17, 1993 [CN] China ................... 93101420

[51] Int. Cl.$^6$ ................ B01D 3/22; B01D 3/38; B01D 3/40; C07C 37/00
[52] U.S. Cl. .............. 422/191; 422/192; 422/194; 422/212; 202/158; 203/DIG. 6; 261/114.1; 568/727
[58] Field of Search ................ 422/189, 190, 422/191, 192, 194, 212; 202/158; 203/DIG. 6; 261/114.1; 568/727

[56] References Cited

U.S. PATENT DOCUMENTS

| | | | |
|---|---|---|---|
| 1,782,862 | 11/1930 | Wagner | 261/114.1 |
| 3,760,006 | 9/1973 | Gammill et al. | 260/619 A |
| 3,802,567 | 4/1974 | Kunz | 210/189 |
| 3,849,076 | 11/1974 | Gryaznov et al. | 23/288 R |
| 3,853,929 | 12/1974 | Cornelius et al. | 260/407 |
| 4,045,379 | 8/1977 | Kwantes et al. | 260/2.2 |
| 4,051,020 | 9/1977 | McDonald | 208/213 |
| 4,096,616 | 6/1978 | Coffinberry | 29/157.3 A |
| 4,124,069 | 11/1978 | Becker | 165/164 |
| 4,307,254 | 12/1981 | Smith, Jr. | 568/697 |
| 4,343,354 | 8/1982 | Weber | 165/165 |
| 4,351,966 | 9/1982 | Flock | 568/753 |
| 4,400,555 | 8/1983 | Mendiratta | 568/728 |
| 4,471,154 | 9/1984 | Franklin | 585/864 |
| 4,536,373 | 8/1985 | Jones, Jr. | 422/211 |
| 4,595,704 | 6/1986 | Fazio | 521/31 |
| 4,624,748 | 11/1986 | Haunschild | 203/29 |
| 4,719,968 | 1/1988 | Speros | 165/154 |
| 4,766,254 | 8/1988 | Faler et al. | 568/724 |
| 4,798,654 | 1/1989 | Iimura et al. | 203/94 |
| 4,820,740 | 4/1989 | Li | 521/32 |
| 4,840,228 | 6/1989 | Shaner | 165/165 |

(List continued on next page.)

FOREIGN PATENT DOCUMENTS

0523931  1/1993  European Pat. Off. .

OTHER PUBLICATIONS

International Search Report for PCT/CN94/00012.
Oct. 10, 1996 European Examination Report for EP 94 907 484.3.

Primary Examiner—Nina Bhat
Attorney, Agent, or Firm—Chilton, Alix & Van Kirk

[57] ABSTRACT

A reactive stripping process for continuously carrying out chemical reactions while separating the reactants from the reaction products is provided. The process comprises passing liquid reactants and an inert stripping gaseous stream in a reactor column (1) having a plurality of perforated trays (2) provided therein and interconnected by a plurality of downcomers (3), screens (4 and 5) provided on the trays (2) and the top openings of the downcomers (3). The trays (2) and downcomers (3) are associated with the screens (4 and 5) to form a chamber optionally provided with a solid particulate or liquid catalyst (6) therein. A reactive stripping apparatus for performing such a process is also provided. According to the invention, at least one reaction product and the reaction mixture having different boiling points can be separated in order that chemical reactions proceed continuously as desired.

18 Claims, 2 Drawing Sheets

U.S. PATENT DOCUMENTS

| | | | |
|---|---|---|---|
| 4,877,087 | 10/1989 | Hill | 165/181 |
| 4,917,769 | 4/1990 | Van Horn | 202/158 |
| 4,918,245 | 4/1990 | Iimuro et al. | 568/727 |
| 4,919,245 | 4/1990 | Braden | 165/10 |
| 4,937,051 | 6/1990 | Graven et al. | 422/194 |
| 4,942,265 | 7/1990 | Iimuro et al. | 568/724 |
| 4,950,804 | 8/1990 | Iimuro et al. | 568/727 |
| 4,950,806 | 8/1990 | Iimuro et al. | 568/724 |
| 4,954,661 | 9/1990 | Iimuro et al. | 568/727 |
| 4,971,139 | 11/1990 | Khattar | 165/86 |
| 5,013,407 | 5/1991 | Nocca et al. | 202/158 |
| 5,026,459 | 6/1991 | Quang et al. | 202/158 |
| 5,075,511 | 12/1991 | Li | 568/727 |
| 5,087,767 | 2/1992 | Okamoto et al. | 568/727 |
| 5,130,102 | 7/1992 | Jones, Jr. | 422/191 |
| 5,133,942 | 7/1992 | Jones | 422/142 |
| 5,158,754 | 10/1992 | Lefers et al. | 422/191 |
| 5,184,675 | 2/1993 | Gardner | 165/184 |
| 5,198,591 | 3/1993 | Kiedik et al. | 568/727 |
| 5,277,847 | 1/1994 | Gentry et al. | 261/114.1 |
| 5,291,989 | 3/1994 | Pinaire et al. | 202/158 |
| 5,338,517 | 8/1994 | Evans, III et al. | 422/191 |
| 5,372,790 | 12/1994 | Shirtum et al. | 422/135 |
| 5,447,609 | 9/1995 | Yeoman et al. | 203/99 |
| 5,510,089 | 4/1996 | Jones | 422/189 |

MULTIPLE STAGE SUSPENDED REACTIVE STRIPPING PROCESS AND APPARATUS

TECHNICAL FIELD OF THE INVENTION

The present invention pertains to a novel reactive stripping process for carrying out chemical reactions in a suspended bed reactor column. In a further aspect, the present invention relates to a novel reactive stripping apparatus for simultaneously performing chemical reactions and reaction product stripping which comprises a plurality of suspended beds. In another aspect, the present invention is directed to a novel process and apparatus for performing simultaneously heterogeneous catalysis and separation or stripping of at least one reaction product from the reaction mixture in a substantially vertical, multiple stage reactive stripping arrangement comprising a plurality of suspended beds which have particulate catalyst supported thereon.

More specifically, the present invention is concerned with a novel process and apparatus for the production of bisphenol-A in a substantially vertical, multiple stage reactive stripping arrangement comprising a plurality of suspended beds which have a particulate solid modified cation-exchange resin catalyst supported thereon whereby successive treatments are substantially simplified, the recycle amount of unreacted reactants is reduced to a great extent and expenditure of capital on equipment and operational costs are decreased greatly.

BACKGROUND ART OF THE INVENTION

It is always an object of industrialization to continuously carry out chemical reactions and to obtain excellent conversion of reactants. To continuously perform many chemical reactions which are reversible or easily achieve reaction equilibrium under practical and economic reaction conditions, it is required to separate the reactants from the reaction products since separation of at least a part of the reaction products form the reaction mixture will allow the chemical reactions to proceed further. As a result, the yield of the desired products is improved according to reaction kinetics. However, great difficulty is usually encountered in trying to continuously remove at least one reaction production, such as, for example, in the preparation of 2,2-bis(4-hydroxyphenyl)propane (bisphenol-A, hereinafter sometimes referred to as "4,4-BPA" or "p,p-BPA" or simply identified as "BPA") which is a basic feedstock or intermediate product for the commercial manufacture of various polymers including the polyarylates, polyamides, polyetherimides, polysulfones and polycarbonates, etc., epoxy resins and modified phenol-formaldehyde resins, etc.

Heretofore, a variety of solutions or proposals have been provided to overcome the difficulty in separating reactants from reaction products while carrying out reactions such as condensation reactions, etherification reactions, amination reactions and saponification reactions, etc. In this respect, it is well known to employ distillation reactor systems such as, for example those as described in U.S. Pat. Nos. 4,471,154 and 5,133,942, etc.

These known distillation reactor systems are conventionally used such that chemical reactions are carried out while the reactants are extremely rapidly separated from the reaction products by fractional distillation because of differences in boiling points thereby allowing the chemical reactions to quickly proceed further as desired. Usually, the known distillation reactor systems are used to carry out heterogenous catalytic chemical reactions in a liquid phase in the presence of a particulate catalyst. In this case, the catalyst particles are completely submerged in the liquid phase under static state to form a fixed bed reactor system or are suspended in the liquid phase by agitation action of a gas to form a suspended bed reactor system.

More particularly, U.S. Pat. NO. 4,215,011 to Lawrence A. Smith, Jr. discloses a catalyst system for use in a reaction-distillation column comprising a plurality of closed cloth pockets containing a particulate catalytic material arranged and supported in said reaction-distillation column by a wire mesh that is intimately associated with said closed cloth pockets. This complicated arrangement of catalytic particles is particularly provided for use in the separation of isoolefins from streams containing mixtures of at least one isoolefin and the corresponding normal olefin. This patent is especially useful for the separation of isobutene from a stream containing normal butenes. It is not known to be useful or to have ever been used in the preparation of bisphenol-A.

U.S. Pat. No. 4,308,404 to Arien Kwantes et al. proposes an improved continuous process for preparing bisphenols from phenol and carbonyl compounds such as bisphenol-A from phenol and acetone in the presence of an acidic ion-exchange resin catalyst in a reaction zone comprising a series of reactors wherein a part of the effluent from at least one reactor with the exception of the last reactor is recycled to the preceding reactor, preferably to the first reactor, and the ratio of the recycled stream to the stream fed to the following reactor (the recycle ratio) is in the range of from about 0.1:1 to about 10:1. Nevertheless, the Kwantes' manner of operation undoubtedly results in a substantial reduction in the reaction rate as the condensation reaction proceeds.

U.S. Pat. No. 4,391,997 to Ashok K. Mendiratta describes a process for the production of bisphenol-A comprising reacting phenol and acetone in the presence of a cation-exchange resin as a catalyst in a continuous reactor system in which the reaction temperatures increases along the length of the reactor or alternatively, the reaction takes place in a series of reactors operated at progressively increasing temperatures to produce a condensation reaction mixture of bisphenol-A, phenol, acetone, water and phenol/acetone condensation reaction by-products which may be then treated by any conventional means to form a bisphenol-A product having limited quantities of coloring substance and other condensation reaction by-products or impurities. It is attempted according to Mendiratta's teachings to reduce the amount of by-products impurities and the material losses, thereby improving the material usage and the quality of BPA in the system employed. However, the conversion and selectivity of the acetone reaction is also remarkably limited. Actually, a phenol to acetone molar ratio of about 10.7:1 and the temperature of about 90° C., the conversion of acetone remains constant at about 69%. Under steady operation conditions, p,p-bisphenol-A is formed in yields of about 94+ percent and p,p-BPA plus o,p-BPA are formed in combination in yields of from about 98+ to about 99+ percent (based on p,p-BPA, o,p-BPA and other minor by-products). The selectivity of p,p-BPA is believed to be possibly as great as only about 96% (based on p,p-BPA, o,p-BPA and other minor by-products).

U.S. Pat. No. 4,400,555 to Ashok K. Mendiratta provides an improved bisphenol-A synthesis reactor system using a multiple acetone injection technique in a cation-exchange resin catalyzed bisphenol-A production process. Ashok K. Mendiratta intends to yield high material usage and to improve bisphenol-A product color or hue as well as to reduce the equipment capital expenditure/operating costs involved with recovery and recycling of excess phenol for the same overall phenol to acetone ratio charged to the reactor system. In operation, 25–75% of the feedstream of acetone is injected to the first reactor or the beginning of the reactor and the remainder is injected to the subsequent reactors or along the length of the reactor and all of phenol is charged to the first reactor or the beginning of the reactor. It is believed that this procedure allows a high relative phenol concentration to be maintained during most of the condensation reaction process while the overall phenol to acetone molar ratio is reduced to be as low as possible. According to Mendiratta, the conversion and selectivity to p,p-BPA of acetone reaction are significantly limited [the yield of p,p-BPA is about 94+ percent and the yield of p,p-BPA and o,p-BPA in combination is only from about 98+ to about 99+ percent (based on p,p-BPA, o,p-BPA and other minor by-products)] by means of the multiple acetone injection system.

U.S. Pat. No. 4,471,154 to Frederick C. Franklin suggests a staged and fluidized bed distillation reactor including a reactor vessel containing a plurality of trays vertically spaced from one another and interconnected by means of respective downcomers for conducting reaction liquid downward from tray to tray, at least some of said trays further containing a quantity of a particulate catalyst which is confined within a containing volume by a screen in connection to each of the trays and fluidized by the action of vapor. When operation is started, a stream of vapor and a stream of liquid pass through the respective trays containing the catalyst thereon upward and downward, respectively. The lower and higher boiling materials are removed from the upper and lower portions of the distillation reactor, respectively. It is evident in view of teachings of Frederick C. Franklin that this patent is focused on conducting a reaction of reactants A and B by providing a staged, fluidized bed distillation reactor.

U.S. Pat. No. 5,087,767 to Kenichi Okamoto et al. suggests a method for preparing 2,2-bis(4-hydroxyphenyl) propane comprising reacting acetone and phenol in the presence of an acidic ion-exchange resin as a catalyst wherein the reaction of acetone and phenol is performed while removing a part of the water generated during the reaction from a mixed solution containing acetone and phenol by a pervaporation method with a selectively water-permeable membrane such as porous glass, silica, alumina and ceramic membranes. According to the method described in this patent, the water generated through the reaction can rapidly be removed simultaneously with or alternatively to the reaction by a pervaporation operation and, therefore, the catalytic activity of the ion-exchange resin is not impaired at all. Moreover, any complicated operations associated with dehydration are not required. Thus, the acidic ion-exchange resin catalyst can continuously be used over a long time period without any treatment for the regeneration thereof. Further, according to the method of this patent, bisphenol-A can be economically prepared from acetone and phenol in a high conversion rate and good yield. However, as shown in the illustrative examples, the capacity of removing water is not strong so that after about 8 ours of the condensation reaction in a batch stirred reactor the conversion of acetone or the yield of p,p-bisphenol-A amounts to about 75% for an inorganic-organic composite membrane, 80% for an organic membrane and 90% for an inorganic membrane.

U.S. Pat. No. 5,133,942 to Edward M. Jones provides and arrangement for concurrently carrying out chemical reactions in a distillation column reactor, separating by fractional distillation the reactants and reaction products, removing the reaction catalyst from a distillation column reactor and replacing the used catalyst with fresh and/or regenerated catalyst. The distillation column contains a plurality of suitable liquid-vapor contact trays. Each of said trays has a downcomer and weir associated therewith, said downcomer connecting each said tray to the tray below each said tray. A solid particulate catalyst is supported on at least a portion of said trays by wire mesh or screen or filter medium and submerged to approximately the depth of the liquid on said trays. The vapor rising through the liquid on the trays tends to keep the particulate catalyst in the form of suspension in the liquid. Obviously, there are a lot of chemical reactions which can not be carried out because the reaction temperature of the reactants and the distillation temperature of the component or product to be seperated out by fractional distillation are not consistent with each other or there is a great difference therebetween.

Obviously, the above-mentioned patents can not be used to perform chemical reactions wherein the effective reaction temperature is lower than the boiling temperature of the reaction mixture.

As an example, the production of bisphenol-A from phenol and acetone in the presence of catalytic ion-exchange resin particles will be hereinafter described in a little more detail.

Reaction and distillation are usually combined in a distillation reactor system to withdraw by fractional distillation one of the reaction products once it is formed during the reaction whereby yields of the desired products or conversion of a feedstream are enhanced to a great extent. Heretofore, fixed bed reactor systems are in general used in the product of bisphenol-A and conversion of acetone is only about 50% by weight in a single pass. Therefore, known distillation reactors have not ever been used in the product of bisphenol-A in order to enhance conversion of acetone and to obtain decrease in energy consumption, recycle quantity, material especially bisphenol-A product loss and volume of equipment.

Though reactive distillation is theoretically considered to be valuable, the practical application of distillation reactor systems is very limited. As a typical example, reactive distillation is used to produce MTBE and low molecular weight esters in distillation reactor system, but is is rarely used in other industries. It has not yet been used in reactions such as amidation, hdyrogenation and methoxylation though it is theoretically applicable thereto. Difficulty is always encountered in that there is great difference between temperatures at which catalyst shows activity and boiling points of reaction mixtures.

For instance, temperatures at which catalyst is active in the condensation reaction for the product of bisphenol-A generally range from about 60° C. to about 100° C. with 130° C. being the highest. At these temperatures and the pressures involved, excess or unreacted phenol and water, etc. can not boil and therefore can not be distilled out from the reaction system. Otherwise, if higher temperatures are used, calalystis susceptible to deactivation or even complete destruction because it may be softened or aged and the like whereas the boiling temperature of the reaction mixture of phenol, reaction products and by-product impurities is higher than 180° C. Obviously, distillation reactor systems are not usable in the product of bisphenol-A. In view of the reaction kinetics, water formed during the condensation reaction suppresses the reaction rate. In known processes, water is taken out from reaction systems using a semipermeable membrane or a dehydrating agent or the like which have been described in the literature such as, for example the above-mentioned patents.

DISCLOSURE OF THE INVENTION

The present invention is intended to overcome the above-mentioned disadvantages by providing a novel reactive stripping process and apparatus.

Accordingly, on object of the present invention is to provide a process for continuously carrying out chemical reactions while separating the reactants from at least one of the reaction products.

Another object of the present invention is to provide a reactive stripping process for simultaneously performing chemical reactions and separating at least one of the reaction products countercurrently from the reactants by stripping the reaction product with an inert gaseous stream in a reactor column having a plurality of vapor-liquid contact trays provided therein which are interconnected by a plurality of downcomers.

A further object of the present invention is to provide a process for continuously stripping at least one lower boiling reaction product from the higher boiling reaction mixture with an inert gaseous stream when performing chemical reactions in a novel multiple stage suspended reactive stripping apparatus comprising a plurality of perforated trays provide din a reactor column and interconnected by a plurality of downcomers wherein at least one of liquid reactants is introduced into the uppermost tray, one or more other reactants are introduced concurrently into some or all of the trays below the upper most tray and the inert gaseous stream is allowed to rise through the perforated trays while taking the lower boiling reaction product out of the reaction mixture.

A still further object of the present invention is to provide an apparatus for continuously carrying out chemical reactions by withdrawing at least one reaction product from the reaction mixture.

A still further object of the present invention is to provide a reactive stripping apparatus for continuously performing chemical reactions concurrently while stripping at least one lower boiling reaction product form the higher boiling reaction mixture with an inert gaseous stream.

A still further object of the present invention is to provide a novel process and apparatus for the production of bisphenol-A from phenol and acetone in good yields and excellent selectivity in a novel reactor column having a plurality of perforated trays provided therein and interconnected by a plurality of downcomers each of which has a screen connected to the top thereof, a screen provided on each tray and a solid particulate catalyst contained in a containing volume defined by a downcomer and the screen in association with a tray whereby all the required phenol is introduced into the uppermost tray and acetone is introduced into some or all of the trays below the uppermost tray in divided portions.

In one aspect according to the present invention, there is provided a reactive stripping process for continuously carrying out chemical reactions while separating at least a lower boiling reaction product from a reaction mixture, the process comprising, (a) allowing liquid reactants to flow concurrently and downwardly in a reactor column having
  (i) a plurality of perforated trays provided therein,
  (ii) a first screen located on each tray, and
  (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a chamber optionally with a catalyst contained therein, in order to form a liquid reaction mixture including at least a lower boiling reaction product, (b) simultaneously allowing an inert gaseous stream to pass upwardly through the trays and chambers for agitating the content of the chambers to form a suspension in the liquid reaction mixture, (c) withdrawing at least the lower boiling reaction product from the upper portion of the reactor column with the inert gaseous stream and, (d) discharging the remainder of the reaction mixture from the lower portion of the reactor column.

In another aspect according to the present invention, there is provided a reactive stripping apparatus for continuously carrying out chemical reactions while separating at least a lower boiling reaction product form a reaction mixture, the apparatus comprising (a) a reactor column having a lower portion and an upper portion with a top, (b) a plurality of perforated trays provided in the reactor column, (c) a first screen located on each tray, (d) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a chamber optionally with a catalyst contained therein, (e) inlets in the upper portion and along the length of the reactor column above the lower most tray for the introduction of liquid and/or vapor reactants, (f) an inlet and an outlet located in the lower portion of the reactor column for introducing the inert gaseous stream and discharging the reaction mixture, respectively, and (g) an outlet at the top of the reactor column for withdrawing the inert gas with at least one lower boiling reaction product from the reaction mixture.

In a further aspect according to the present invention, there is provided a reactive stripping process for the production of high purity or polycarbonate grade and ultrapure bisphenol-A comprising (1) reacting from about 4 to about 12 times molar excess of phenol and acetone in the presence of a modified cation-exchange resin as a catalyst in a reactor column having
  (i) a plurality of perforated trays provided therein,
  (ii) a first screen located on each tray,
  (iii) a plurality of downcomers interconnecting the trays, each of the downcomers having a second screen connected to the top thereof, the second screen, a portion of each said downcomer, a portion of the side wall the reactor column and one of the perforated trays with the first screen thereon in combination defining a catalyst chamber,
  (iv) a solid particulate catalyst contained within the catalyst chamber at a temperature in the range of from about 60° C. to about 130° C. in which process all of the phenol necessary for the condensation reaction thereof with acetone is charged to the reactor column from above the uppermost tray, portions of all the required acetone are charged to the tray next to the uppermost tray and some or all of lower trays, respectively, and an inert gaseous stream is upwardly passed through the catalyst chambers to form solid-liquid suspensions and to strip water from the reaction mixture, (2) cooking the liquid condensation reaction mixture effluent from the reactive stripping apparatus in a crystallizer to form a slurry containing crystals of the adduct of bisphenol-A and phenol in 1:1 molar ratio and the mother liquor, (3) separating the adduct crystals from the mother liquor optionally followed by washing the separated adduct crystals, (4) subjecting the adduct crystals obtained in step (3) above to phenol removal operation to obtain a high purity bisphenol-A crystals, optionally followed by (5) recrystallizing the high purity bisphenol-A crystals obtained in step (4) above in the presence of solvent in a recystallizer, (6) separating the bisphenol-A crystals from the mother liquor optionally followed by washing the separated bisphenol-A crystals to obtain an ultrapure bisphenol-A product.

The apparatus used for the operation of reactive stripping according to the present invention is also referred to as multistage suspended bed for the reactive stripping. According to the present invention, the apparatus includes a reactor column containing a plurality of trays vertically spacedly from one another. The trays are interconnected by downcomers for conducting liquid downward from tray to tray. Sieve screens are placed on every tray, and a solid particulate catalyst having a diameter more than the sieve mesh of the screen is carried on the sieve screens directly. The top opening of the downcomers are enclosed or covered with the same sieve screens, preferably at the top of each downcomer. An inert gaseous stream enters the reactor column from the gas inlet at the reactor bottom, rises upwardly through the liquid layers on the trays, and leaves from the gas outlet at the reactor top. The reactor column has at least one liquid feedstream inlet at the reactor top, and there are several side feedstream inlets at different heights along the wall of the reactor column above the lower most tray. There is a liquid product outlet at the bottom of the reactor column. Along the side of the reactor there is a side pipe for each tray to withdraw the used or deactivated catalyst and introduce fresh and/or regenerated catalyst. The trays provided in the reactive stripping column are sieve trays, float valve trays or any other suitable gas-liquid contact trays.

The continuous process of reaction between phenol and acetone for preparing bisphenol-A in the presence of an ion-exchange resin as a catalyst according to the invention is characterized in that the reaction is performed in a novel multiple stage (bed) reactive stripping apparatus instead of the fixed-bed reactor. All of phenol necessary for the reaction is charged from the liquid feedstream inlet in the upper portion of the reactor and acetone is charged from the several side feedstream inlets. Use of the novel reactive stripping apparatus overcomes the aforementioned disadvantages.

According to the present invention, the effect of the inert gas or gaseous stream, the perforated trays, and side acetone inlets may be summarized in a preferred embodiment of the present invention for performing the reaction between phenol and acetone as follows;

The effect of the ring inert gas is to prevent leakage of the reaction liquid through the sieve screens which are located on the trays thereby maintaining a certain height of the reaction liquid on each tray and quickly reacting phenol and acetone on the trays, to allow the resin catalyst particles to be suspended in the reaction liquid layers on the trays owing to the agitation of the inert gas so that each tray is equal to an ideal mixing tank, the whole reactor being equal to a lot of tanks in series, and to remove water generated during the reaction between phenol and acetone with the inert gas through bubble contact of the inert gas with the reaction liquid.

The effect of the perforated trays is to confine the backmixing zone of the reaction liquid to one tray, thereby fully utilizing the higher reaction rate of the beginning or upper trays, to supply the required gas-liquid mass transfer area in order to remove water generated during the reaction from a mixed solution containing acetone, phenol and bisphenol-A product, and to reduce the static liquid level on the trays, thereby allowing the resin particles to be uniformly suspended in the liquid.

The effect of the several side inlets for acetone feedstream is to maintain a high relative phenol concentration in individual chambers whereas the overall phenol/acetone feed molar ratio is relatively low, thereby enhancing the reaction selectivity to bisphenol-A and reducing the phenol recycle amount, and to allow higher reaction temperatures to be employed.

BEST MODE FOR CARRYING OUT THE INVENTION

Figure 1:
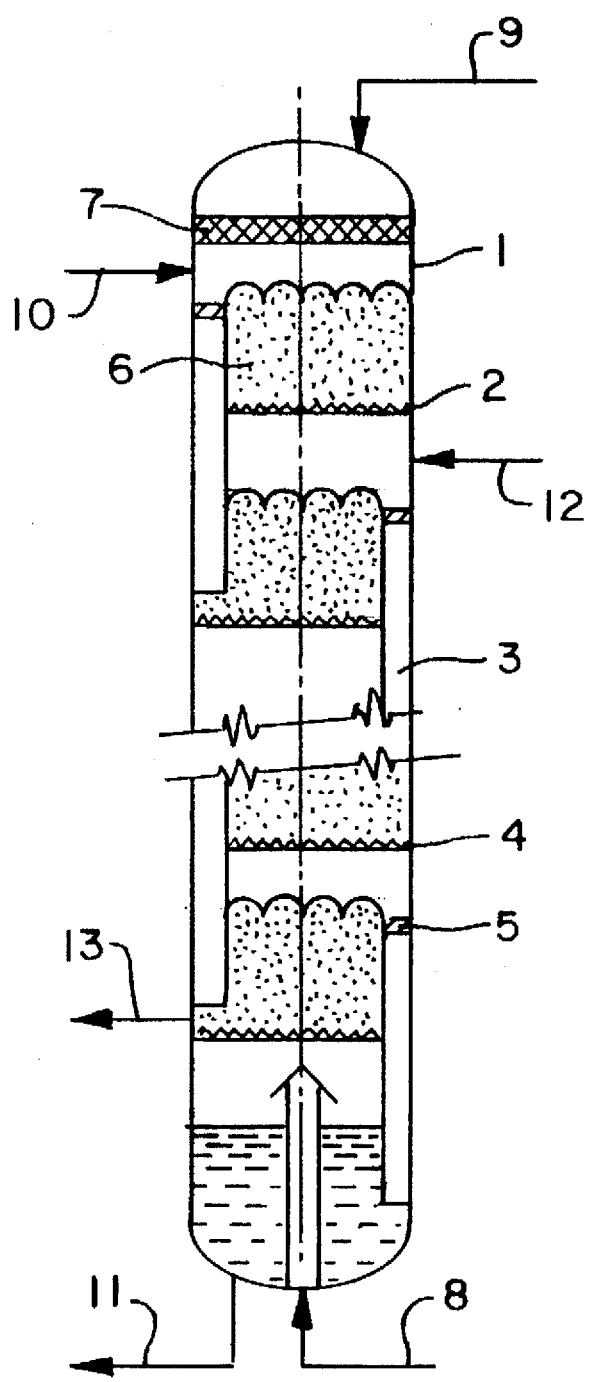
FIG. 1 is a schematic diagram of a novel multiple stage suspended reactive stripping apparatus showing various trays having a particulate catalyst supported on each tray according to the present invention.

Referring first to FIG. 1, the novel multiple stage suspended reactive stripping apparatus for continuously carrying out chemical reactions while separating at lease one lower boiling component from the reaction mixture or the reaction system includes a reactor column 1 with a plurality of vertically spaced trays 2. A downwardly flowing liquid flow path is provided between the trays by downcomers 3. Sieve screens 4 are placed on the trays, all of the top openings of the downcomers are enclosed by the same sieve screens 5 as those placed on the trays. Sieve screens 4 and 5 are constructed of, for example, stainless steel, or another material which will not be affected under the reaction conditions. Particulate catalyst 6 (shown in the suspended state) having a larger diameter than the sieve mesh is located on the trays. There is a liquid entrainment catching structure 7 in the upper section of the reactor column. No. 8 and No. 9 designate the inert gas inlet and outlet, respectively. No. 10 and No. 11 designate the liquid reactant inlet and liquid reaction mixture outlet, respectively. Along the reactor side wall there are several side reactant inlets 12 and a side pipe 13 for withdrawing the used particulate catalyst from each tray and charging fresh particulate catalyst and/or the regenerated catalyst.

As shown in FIG. 1, there are at least two perforated trays 2 in the reactor column. Of course, the more trays 2 are used, the better efficiency will be obtained but the expenditure of capital on the equipment will be thus increased. The porosity of the trays 2 is usually from about 5 to about 50%, preferably from about 10 to about 30%. The mesh of the screens 4 depends on the particle size of the particulate catalyst 6 but the former is always slightly smaller than the latter. The downcomers 3 all have the screen caps 5 located on the ends thereof and the caps 5 may be connected to the downcomers 3 in any conventional manner such as by means of welding. The cap screens 5 are constructed from the same materials as the screens 4 which are placed on the trays 2. The length of each downcomer 3 above the tray associated therewith is from about ½ to about ¾ of the height between adjacent two trays 2.

The pressure in the reactor column is atmospheric pressure or a elevated pressure. The proportions of various portions of acetone respectively charged to the reactor column 1 are determined depending predominantly on the desired yields of and selectivity to bisphenol-A. The number of trays 2 above which acetone is charged or the number of the side acetone inlets also depend on the desired yields of and selectivity to bisphenol-A. Of course, the more the acetone inlets, the more complicated the structure of the reactor column. In a preferred embodiment of the present invention, there is at least one tray 2 between two adjacent side acetone inlets though it is possible to provide an acetone inlet above every tray 2. More preferably, there are from 1 to 5 trays between two adjacent side acetone inlets in the practice of the present invention. The acetone feedstream may be in the form of vapor or liquid or mixture thereof.

The inert gaseous stream useful for taking at least one lower boiling reaction product out of the reaction mixture may be any commercially available inert gas such as nitrogen or argon or any mixture thereof and nitrogen is particularly preferred because of availability and economy.

With respect to the manner of carrying out the reactive stripping process according to the present invention, the production of bisphenol-A is in particular exemplified in order to clarify the operation of the apparatus according to the present invention though it is obvious that the present invention may be used to perform a variety of chemical reactions such as amination, hydrogenation, esterification, etherification, methoxylation, saponification and the like.

Figure 2:
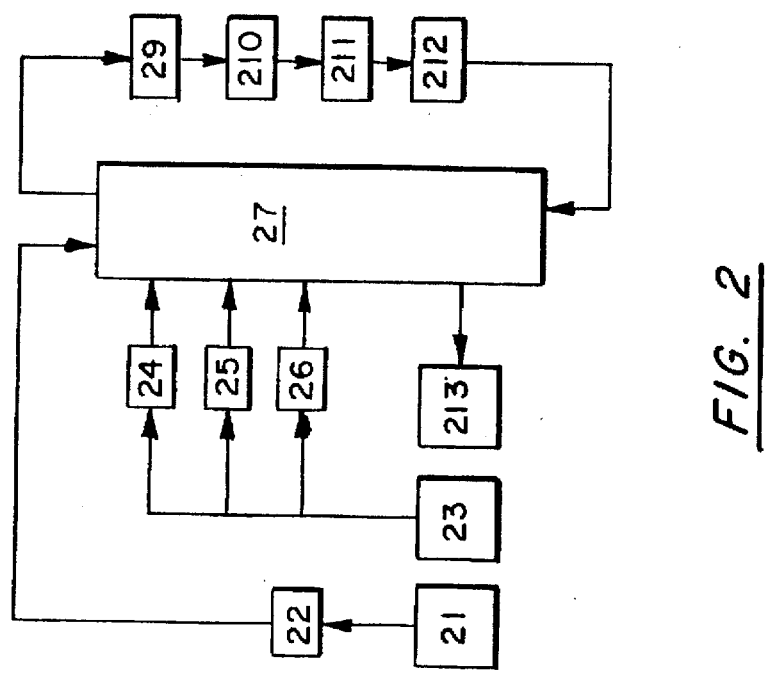
FIG. 2 is a schematic flow diagram for illustrating a preferred embodiment of the present reactive stripping process using a novel apparatus according to the present invention.

Referring to FIG. 2, in a preferred embodiment of the present invention, all phenol necessary for the condensation reaction from a phenol reservoir 21 is charged at the top feed inlet of the reactive stripping reactor column 27 by a phenol pump 22, and acetone is charged to the the reactive stripping reactor column 27 from an acetone reservoir 23 through three side feed inlets by acetone pumps 24, 25 and 26, respectively. Nitrogen is blown into the reactive stripping reactor column 27 from the gas inlet at the reactor bottom by a compressor 212. After leaving the reactive stripping reactor column 27 from the gas outlet at the reactor top, nitrogen passes through a gas-liquid separator 29, a cooling pond 210 and molecular sieve drier 211 and then finally recycled to the reactive stripping reactor column 27 by the compressor 212. The condensation reaction liquids transported to the adduct crystallizer directly by a pump 213.

In accordance with the reactive stripping process of the present invention the overall phenol/acetone feed molar ratio may be about 4–12:1, more preferably is about 7–10:1 and most preferably is about 7:1. The reaction temperature may be from about 60° C. to about 130° C., preferably from about 80° C. to about 100° C. and the residence time calculated on the basis of dry catalyst weight is about 0.25–2 hrs. The reaction pressure is atmospheric or an elevated pressure. The velocity of the rising inert gas is from about 0.006 to about 0.075 m/s based on the area of the column cross-section. The catalyst loading for each tray or chamber is in the range of from about 3% to about 30% by volume of the total volume of the whole mixture including the catalyst and reaction liquid.

Figure 3:
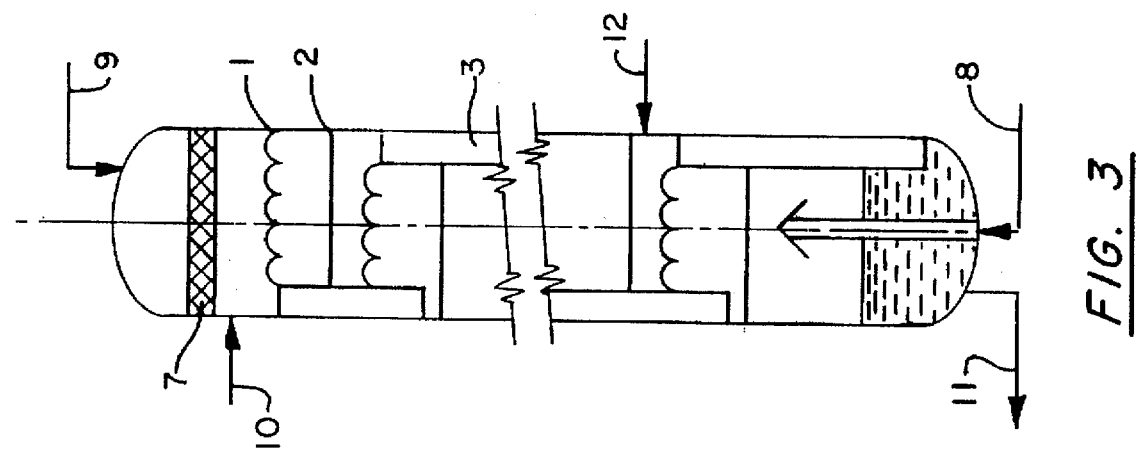
FIG. 3 is a schematic diagram of a second embodiment of a novel multiple stage suspended reactive stripping process and apparatus according to the present invention adapted for use with a liquid catalyst or no catalyst supported on each tray.

The reactive stripping process and apparatus as shown in FIG. 3 are almost the same as those shown in FIG. 1 except that a liquid catalyst is used, and the catalyst is supported on the perforated trays by the rising action of the inert gaseous stream. In FIG. 3, all the same parts constituting the apparatus and feedstreams for carrying out the process as those shown in FIG. 1 are represented by the same numerals. In the embodiment of FIG. 3, however, the screens 4 and 5 as shown in FIG. 1 are essentially unnecessary and therefore are not included in the embodiment which is shown. Furthermore, if no catalyst is used, the side pipe 13 is unnecessary. The manner of operating the apparatus as shown in FIG. 3 is substantially the same as depicted in FIG. 2.

The inert gaseous stream from the gas inlet 8 flows countercurrently relative to liquid streams which enter through liquid reactant inlet 10 and side reactant inlets 12. The reaction between excess phenol from liquid reactant inlet 10 and acetone from side reactant inlet 12 takes place in the liquid-solid suspensions on the trays 2. The above-described multiple stage reactive stripping process and apparatus according to the present invention have the following advantages:

Due to the stir of the inert gas, the particulate catalyst is suspended in the reaction liquid in the reactor column, so the resistance to the diffusion of reactants toward the catalyst surface is reduced and the reaction rate is increased greatly.

The inert gas removes water from the reaction liquid, and as a result, the catalyst maintains a high activity an the reaction rate is further increased. In contrast, in a conventional system, water will poison the catalyst.

Use of multiple acetone injection points in the ion-exchange resin catalyzed BPA synthesis process allows a high relative phenol concentration to be maintained at each individual tray in order that high purity and ultrapure BPA can be prepared at a lower overall phenol/acetone feed molar ratio.

The stirring effect and heat transfer effect of the inert gas can reduce the column's axial and diametrical temperature differences brought about by exothermal reaction, so local overheating can be avoided and the optimum reaction conditions can be controlled easily.

For each tray of the reactor column there optionally, can be a side pipe by which the resin can be added to or removed from the tray. Thus, the catalyst can be changed tray by tray, and it is therefore unnecessary to have a spare column. Furthermore, it is possible to operate the column continuously even when the catalyst on one tray is being changed.

In accordance with the present invention, a condensation reaction liquid with a high BPA concentration is obtained. This liquid can be directly transported to a crystallizer to produces slurry of 1:1 molar ratio phenol/BPA adduct crystals in mother liquor. Thus, before the crystallization, the operation of removing acetone, water and some phenol in a concentrator by evaporation can be eliminated from the BPA production process. This elimination results in a substantial increase in the quality of the bisphenol-A product.

The lower overall phenol/acetone feed molar ratio reduces the volume of the unreacted phenol recycle stream, and therefore, the burden for the process after the condensation reaction is lightened.

The requirement for a suitable pair of the liquid boiling point and catalyst activity temperatures imposes limits on the efficient use of a distillation reactor column. According to the present invention, because of the more volatile component is removed from the reaction liquid by an inert gas, there is no requirement for a temperature match for the reaction and separation processes.

In accordance with the process of the present invention, the BPA concentration in the condensation reaction liquid can reach 30% by weight or more, the conversion of acetone may be about 96% or more, and the selectivity to BPA may be about 95% or more on the average in a single pass.

The following specific example illustrates the reactive stripping process and the apparatus of this invention.

sieve drier id externally connected to the reactor column for removal of water entrained in the nitrogen stream taken out of the column. Under steady state, the operation conditions are as follows;

| | |
|---|---|
| Reaction temperature | 80° C. |
| Phenol/acetone feed molar ratio | 7:1 |
| Residence time (based on dry catalyst weight) | 0.38 h |
| Flow rate of acetone | 0.49 kg/h |
| Flow rate of phenol | 5.604 kg/h |
| First/second/third acetone injection proportions | 40/40/30% |
| Flow rate of nitrogen | 2.9 m$^3$/h |

The effluent from the reactor bottom was collected and analyzed.

High pressure liquid chromatography and Kari-Fisher water analyzer were used in the analysis of the effluent from the reactor column for composition. The composition of the condensation reaction mixture obtained after operating the reactor column under the steady operation conditions for 12 hours are set out in Table 1.

| example No. | compostion of condensation liquid (wt %) | | | | | | | acetone conversion | selectivity to BPA(%) |
|---|---|---|---|---|---|---|---|---|---|
| | phenol | BPA | Dianins | isomer | BPA-x | water | others | | |
| 4-21 | 69.76 | 29.35 | 0.0663 | 0.519 | 0.286 | 0.276 | 0.138 | | |
| 4-22 | 70.25 | 29.51 | 0.0690 | 0.615 | 0.358 | 0.19 | 0.134 | | |
| 4-23 | 69.34 | 29.21 | 0.0884 | 0.673 | 0.316 | 0.19 | 0.125 | | |
| 4-24 | 60.10 | 29.54 | 0.0803 | 0.682 | 0.323 | 0.17 | 0.147 | | |
| 5-1 | 67.32 | 30.56 | 0.0796 | 0.691 | 0.332 | 0.33 | 0.142 | | |
| 5-2 | 53.34 | 29.12 | 0.1050 | 0.726 | 0.325 | 0.09 | 0.153 | | |
| 5-3 | 53.72 | 29.12 | 0.0832 | 0.712 | 0.328 | 0.17 | 0.155 | | |
| 5-4 | 70.18 | 27.34 | 0.1140 | 0.323 | 0.373 | 0.33 | 0.178 | | |
| 5-5 | 70.50 | 27.78 | 0.0884 | 0.717 | 0.328 | 0.13 | 0.179 | | |
| 5-6 | 70.94 | 29.43 | 0.0707 | 0.511 | 0.286 | 0.31 | 0.014 | | |
| 5-7 | 70.53 | 28.46 | 0.0750 | 0.577 | 0.310 | 0.19 | 0.124 | | |
| average | 69.94 | 29.16 | 0.0837 | 0.886 | 0.323 | 0.22 | 0.135 | 95.3 | 95.5 |

Example

The reactor column of the multiple stage suspended reactive stripping apparatus is made of a glass tube, its internal diameter is about 150 mm, and total height is about 2900 mm. There are thirteen trays on which sieve screens of mesh 60 are placed. The downcomers having an external diameter of about 14 mm and thickness of about 2 mm made of alloy steel 3161 were used. The catalyst used in the reactor column is macroporous sulfonated polystyrene divinyl benzene copolymer ion-exchange resin partially neutralized with mercaptoethylamine. The catalyst load on each tray is about 180 grams on dry weight basis. A molecular The same reactor as described in the above example of the present invention and the same process conditions were used except that the molecular sieve drier 211 was eliminated from FIG. 2. After the operation arrived at the steady state, the condensation reaction mixture discharged from the bottom of the reactor column was analyzed for composition. The composition of the condensation reaction mixture is set out in Table 2.

| composition of condensation liquid (wt %) | | | | | | | Acetone | Selectivity |
|---|---|---|---|---|---|---|---|---|
| Phenol | BPA | Ofanin's | isomer | BPA-X | Water | Other | conversion (%) | to BPA (%) |
| 79.15 | 18.18 | 0.0571 | 0.461 | 0.142 | — | 0.0685 | 59.62 | 95.77 |

Industrial Applicability

In addition to the production of bisphenol-A as hereinabove described, it will be obvious to those of ordinary skill in the reaction engineering, chemical processing and related arts that the present invention may be used to carry out a variety of chemical reactions wherein at least one lower boiling reaction product preferably at least one reaction product needs to be seperated from the higher boiling reaction mixture irrespective of temperature match for the reaction and the separation. As examples of chemical reactions, there may be mentioned amination, saponification, hydrogenation, etherification, esterification, alkylation, etc.

Further, the present invention is hereinbefore described for purposes of explanation and illustration, according to a particularly preferred embodiment for the production of high purity and ultrapure bisphenol-A. It will be apparent to those skilled in the art that many modifications and changes in connection with the general reactive stripping process and apparatus may be made within the scope and spirit of the present invention as generally defined in the following appended claims.

We claim:

1. A reactive stripping process for continuously carrying out chemical reactions while separating the reactants from at least one of the reaction products in a reactor column, the process comprising:
   (a) allowing liquid reactants to flow concurrently and downwardly in a reactor column having a side wall and having:
      (i) a plurality of perforated trays provided therein, and
      (ii) a plurality of downcomers interconnecting the trays, a portion of each said downcomer, a portion of the side wall of the reactor column and one of the perforated trays in combination defining a chamber with a catalyst contained therein in order to form a liquid reaction mixture including at least a lower boiling reaction product, said reactor column additionally having, when the catalyst is other than a liquid catalyst, a first screen located on each tray and each of the downcomers having a second screen connected to the top thereof,
   (b) simultaneously allowing a nitrogen stream to pass upwardly through the trays and chambers for agitating the content of the chambers, wherein, when the catalyst is other than a liquid catalyst, a suspension of the catalyst is formed in the liquid reaction mixture,
   (c) withdrawing at least the lower boiling reaction product from an upper portion of the reactor column with the nitrogen stream, and
   (d) discharging the remainder of the reaction mixture from a lower portion of the reactor column.

2. A reactive stripping process according to claim 1 wherein the catalyst is a solid particulate catalyst.

3. A reactive stripping process according to claim 1 wherein the catalyst is a liquid catalyst.

4. A reactive stripping process according to claim 1 wherein the velocity of the rising nitrogen stream is in the range of from about 0.006 to about 0.075 m/s.

5. A reactive stripping process according to claim 1 wherein liquid reactants are introduced into the reactor column through several inlets.

6. A reactive stripping process according to claim 1 wherein at least one reactant is introduced into the reactor column through several inlets provided at different heights of the column above the lowermost tray.

7. A reactive stripping process according to claim 1 wherein the nitrogen stream which is the entrained substance has been removed from the upper portion of the reactor column with at least the lower boiling reaction product is purified and is recycled to the bottom of the reactor column.

8. A reactive stripping apparatus for continuously carrying out chemical reactions while separating at least a lower boiling reaction product form a reaction mixture, the apparatus comprising:
   (a) a reactor column having a lower portion and an upper portion with a top,
   (b) a plurality of perforated trays provided in the reactor column, the porosity of the trays being from about 5 to about 50%,
   (c) a plurality of downcomers interconnecting the trays, the length of each downcomer above the tray associated therewith being from about ½ to about ¾ of the height between the tray associated therewith and the adjacent tray which is positioned above the downcomer, a portion of each said downcomer, the tray associated therewith and a portion of the side wall of the reactor column, in combiantion defining a chamber,
   (d) inlets in the upper portion and along the side wall of the reactor column above the lower most tray for the introduction of liquid reactants,
   (e) an inlet and an outlet located in the lower portion of the reactor column for introducing a nitrogen stream and discharging the reaction mixture, respectively, and
   (f) an outlet at the top of the reactor column for withdrawing the nitrogen stream with at least one lower boiling reaction product from the reaction mixture.

9. A reactive stripping apparatus according to claim 8 wherein the column trays are sieve trays or float valve trays.

10. A reactive stripping apparatus according to claim 8 wherein each chamber contains solid catalyst particles and the trays have screens placed thereon with a mesh which is smaller than the particle size of the catalyst particles.

11. A reactive stripping apparatus according to claim 8 wherein the apparatus contains catalyst particles and the catalyst load for each tray provided in the reactor column is in the range of from about 3% to about 30% by volume of the total volume of the whole mixture including the catalyst and reaction liquid.

12. A reactive stripping apparatus according to claim 8 wherein the porosity of the perforated trays is from about 10% to about 30%.

13. A reactive stripping apparatus according to claim 8 wherein the screens on the trays are of the same type as the screens connected to the top of the downcomers.

14. A reactive stripping apparatus according to claim 8 wherein a catalyst is contained in the chambers.

15. A reactive stripping apparatus according to claim 14 wherein a first screen is located on each tray and a second screen is connected to the top of each downcomer when the catalyst is other than a liquid catalyst.

16. A reactive stripping apparatus according to claim 8, wherein the reactor column includes a first screen located on each tray and a second screen connected to the top of each of the downcomers, the second screen, a portion of each said downcomer, a portion of the side all of the reactor column and one of the perforated trays with the first screen thereon in combination defining the chamber.

17. A reactive stripping apparatus according to claim 16, wherein the chamber contains a solid particulate catalyst.

18. A reactive stripping process for the production of a reaction mixture having a high bisphenol-A concentration by reacting excess phenol with acetone in the presence of catalyst wherein from about 4 to about 12 times molar excess of phenol is reacted with acetone in the presence of a modified cation-exchange resin catalyst in the form of a particulate solid in a substantially vertical, multiple stage suspended reactive stripping apparatus comprising a reactor column with a side wall, the reactor column having:
 (i) a plurality of perforated trays provided therein,
 (ii) a first screen located on each tray,
 (iii) a plurality of downcomers interconnecting the trays, each of the downcomers having a second screen connected to the top thereof, the second screen, a portion of each said downcomer, a portion of the side wall of the reactor column and one of the perforated trays with the first screen thereon in combination defining a catalyst chamber, and
 (iv) a solid particulate catalyst contained within the catalyst chamber, the reactive stripping process taking place at a temperature in the range of from about 60° C. to about 130° C. in which process all of the phenol necessary for the condensation reaction thereof with acetone is charged to the reactor column from above the uppermost tray, portions of all the required acetone are charged to the tray next to the upper most tray and some of all of lower trays and a nitrogen stream is upwardly passed through the catalyst chambers to form solid-liquid suspensions and to strip water from the reaction mixture.

\* \* \* \* \*

UNITED STATES PATENT AND TRADEMARK OFFICE
CERTIFICATE OF CORRECTION

PATENT NO. : 5,679,312
DATED : October 21, 1997
INVENTOR(S) : Jin et al.

It is certified that error appears in the above-identified patent and that said Letters Patent is hereby corrected as shown below:

Column 13, lines 64 - 65, delete "the entrained substance has been".

Column 14, line 17, delete ","
also, delete "combiantion" and insert --combination--.

Column 14, line 56, delete "all" and insert --wall--.

Signed and Sealed this

Sixth Day of January, 1998

Attest:

BRUCE LEHMAN

Attesting Officer

Commissioner of Patents and Trademarks